US00PP14187P29

(12) United States Plant Patent
Hofmann

(10) Patent No.: US PP14,187 P2
(45) Date of Patent: Sep. 30, 2003

(54) GERANIUM PLANT NAMED 'PACVICA'

(50) Latin Name: *Pelargonium×hortorum (zonal geranium)*
Varietal Denomination: 'Pacvica'

(75) Inventor: Christa Hofmann, Grossdittmannsdorf (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/292,158

(22) Filed: Nov. 12, 2002

(51) Int. Cl.[7] ..... A01H 5/00
(52) U.S. Cl. ..... Plt./327
(58) Field of Search ..... Plt./327, 330

*Primary Examiner*—Kent Bell
(74) *Attorney, Agent, or Firm*—Webb Ziesenheim Logsdon Orkin & Hanson PC

(57) ABSTRACT

A new and distinct zonal geranium plant with distinctive brilliant red-orange colored flowers above medium green foliage with strong zonation.

2 Drawing Sheets

Botanical classification: *Pelargonium×hortorum* (zonal geranium).
Varietal denomination: 'Pacvica'.

BACKGROUND OF THE INVENTION

The present invention comprises a new and distinct cultivar of geranium known by the varietal name 'Pacvica'. The new variety was discovered as a seedling in a selective breeding program in Dresden, Germany. The new variety is the result of a combination breeding of unnamed, unpatented selections from breeding group 8K-34. Plants of the new variety exhibit the flower color and zonation of their parents, but differ in their habit and branching. The new variety was first asexually reproduced by cuttings in Dresden, Germany in 1999. The new variety has been trial and field tested and has been found to retain its distinctive characteristics and remain true to type through successive propagations.

DESCRIPTION OF THE DRAWING

The accompanying photographic drawings illustrate the new variety, with the color being as nearly true as is possible with color illustrations of this type.

DESCRIPTION OF THE PLANT

Figure 1:
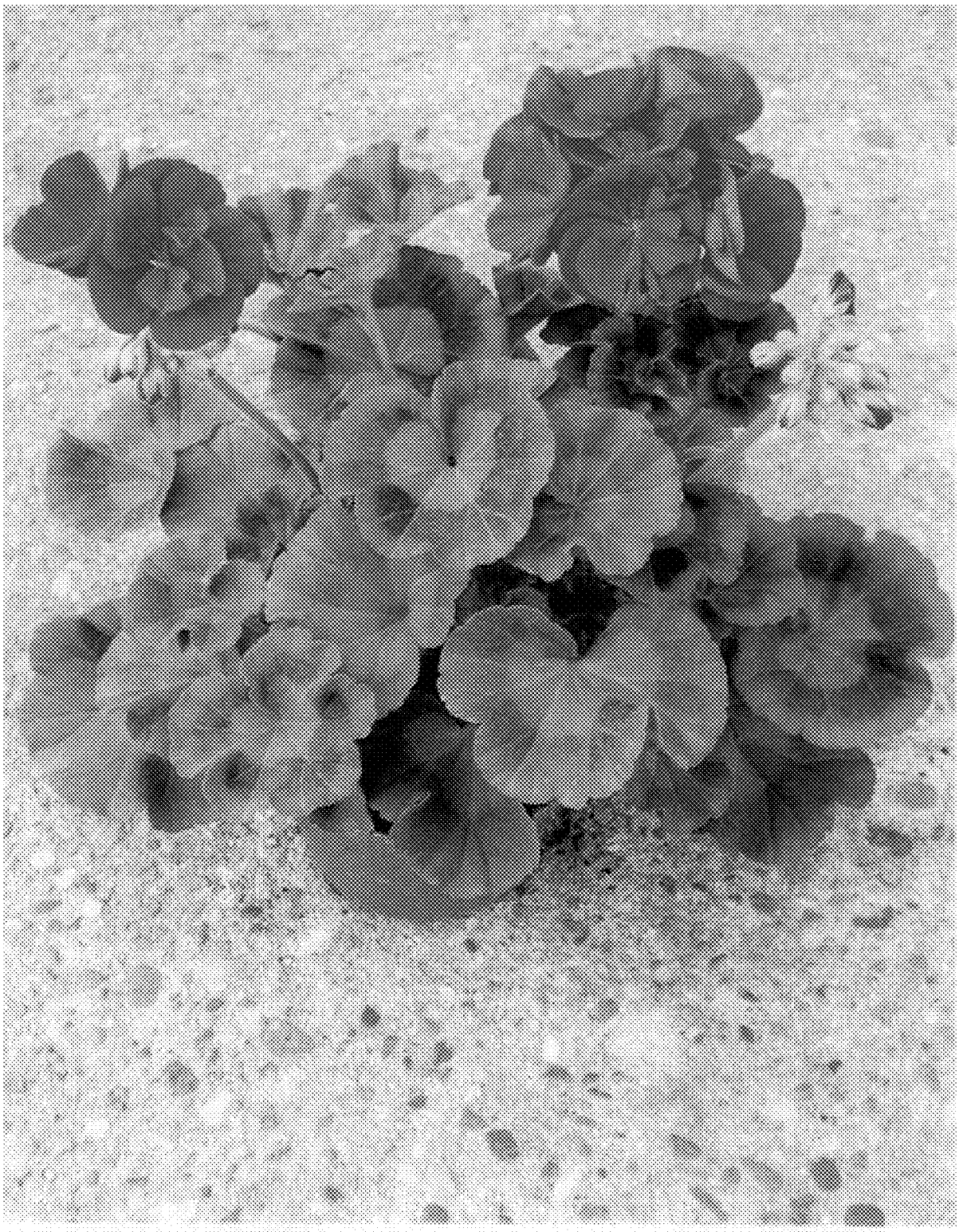
FIG. 1 is a photograph of the plant.
Figure 2:
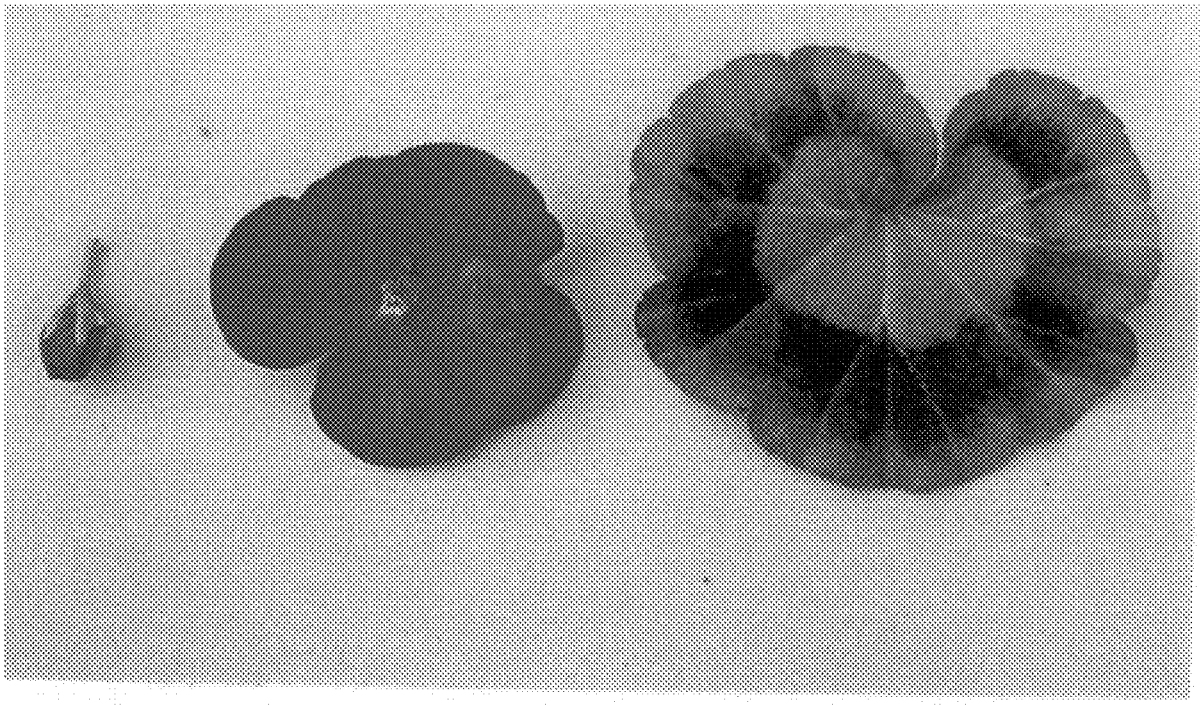
FIG. 2 is a photograph of a bud, flower, and leaf.

The following detailed description sets forth the characteristics of the new cultivar. The data which defines these characteristics were collected from plants propagated in January, potted in February, and grown in a greenhouse and then outdoors in June for data collection in Dresden, Germany. Plants were 9 months old when described. The color readings were taken on a plant under natural indoor light. Color references are primarily to the R.H.S. Colour Chart of The Royal Horticultural Society of London.

PLANT

Form: Upright.
Height: About 17 cm from media surface to top of foliage; about 21 cm from media surface to top of umbels.
Strength: Does not require artificial support.

Growth: Erect, compact, well-branched, continuous flowering.
Roots: White; adventive; 3.5 weeks to develop.
Leaves:
- *Arrangement.*—Opposite.
- *Size.*—Length: 4.3–6.0 cm. Width: 7–10 cm.
- *Shape.*—Overall: Reinform. Base: Nearly closed. Apex: Rounded.
- *Margin.*—Bicrenate.
- *Texture.*—Pubescent.
- *Color.*—Upper surface: 137B. Lower surface: 138B. Zonation: 137A.
- *Ribs and veins.*—Venation: Net-like. Color: 143C.

Petioles:
- *Color.*—144B.
- *Length.*—7–9 cm.

Stem:
- *Color.*—145A.
- *Overall stem length.*—About 14 cm.
- *Internode length.*—1–1.3 cm.
- *Lateral branch length.*—7–8 cm.

THE BUD

Shape when closed:
- *Overall.*—Spherical.
- *Individual bud.*—Elliptical.

Size when closed:
- *Overall.*—About 4 cm across cluster.
- *Individual bud.*—1.3 cm long, 0.9 cm wide.
- *Color.*—40A.

INFLORESCENCE

Size of umbel:
- *Width.*—About 9–10 cm.
- *Length.*—About 9–10 cm.
- *Depth.*—9–10 cm.

Borne: Umbel; Flower on pedicel, pedicel on peduncle.
Flowers:
- *Form.*—Zygomorph.
- *Number of flowers per umbel.*—20–22.
- *Size.*—Diameter: About 4.8–5.2 cm. Depth: About 1.8 cm.

Petals:

*Color.*—Upper surface: 40A. Lower surface: 43B. Shape: Overall: Round to oval. Base: Pointed. Apex: Rounded. Size: 2.6–2.8 cm long; 2.3–2.6 cm wide. Margin: Entire. Number per flower: About 8. Texture: Smooth.

Sepals:

*Color.*—Upper surface: 144B. Lower surface: 144B.

*Shape.*—Overall: Narrow, pointed. Apex: Pointed. Base: Wider than apex, pointed.

*Size.*—Length: About 1.0–1.1 cm. Width: About 0.3 cm.

Petaloids:

*Quantity.*—0–3.

*Shape.*—Irregular.

*Color.*—40A upper surface, 43B lower surface.

Pedicel:

*Length.*—1.8–2.2 cm.

*Color.*—Ranges between 175B and 143A.

Peduncle:

*Length.*—About 17 cm.

*Color.*—143A.

*Lastingness of umbel.*—About 3–4 weeks.

Natural flowering season: Blooms continuously throughout summer; plants last until frost.

Disease/pest resistance: No susceptibility to diseases or pests has been noted to date.

REPRODUCTIVE ORGANS

Stamens:

*Anthers.*—0.1–0.2 cm. in length.

*Filaments.*—Length: 0.7–0.8 cm. Color: 27D. Pollen: 25A, abundant.

Pistils:

*Number.*—One.

*Length.*—About 0.9 cm.

*Stigma.*—41B.

*Style.*—Length: 0.2 cm. Color: 53C.

*Ovaries.*—Superior, pubescent, about 0.2 cm long, 140B.

Seeds: Rarely present; if present, 5 per flower, 0.4 cm long, colored 165A.

GENERAL CHARACTERISTICS

1. Brilliant red-orange color.
2. Strong foliage zonation.
3. Semi-double flower.
4. Heat tolerant.
5. Tetraploid.
6. High yield of cuttings.
7. Rich flowering.
8. Long-lasting.
9. Well-branched, compact growth.

I claim:

1. A new and distinct variety of geranium plant substantially as shown and described.

* * * * *